United States Patent [19]

Müller et al.

[11] Patent Number: 4,537,714
[45] Date of Patent: Aug. 27, 1985

[54] PROCESS FOR THE PREPARATION OF LOWER ALKYL ESTERS OF N-L-α-ASPARTYL-L-PHENYLALANINE AND OF NEW INTERMEDIATES FOR THEIR PREPARATION

[75] Inventors: Hans-Rudolf Müller, Schaffhausen; Heinrich Bollinger, Beringen, both of Switzerland

[73] Assignee: Eprova Ag Forschungsinstitut, Schaffhausen, Switzerland

[21] Appl. No.: 511,672

[22] Filed: Jul. 7, 1983

[30] Foreign Application Priority Data

Jul. 20, 1982 [CH] Switzerland .................. 4433/82
Jan. 20, 1983 [CH] Switzerland .................. 4433/82

[51] Int. Cl.$^3$ ............................................. C07C 103/52
[52] U.S. Cl. ............................................. 260/112.5 R
[58] Field of Search ................................. 260/112.5 R

[56] References Cited

U.S. PATENT DOCUMENTS 3,492,131  1/1970  Schlatter et al. ............ 260/112.5 R
4,332,718  6/1982  Takahashi et al. ........... 260/112.5 R

FOREIGN PATENT DOCUMENTS 0035047  9/1981  European Pat. Off. .
0099960  2/1984  European Pat. Off. .

OTHER PUBLICATIONS

*Helvetica Chimica Acta*, vol. XLIV, Helvetica Chimica Acta, Basel, 1961, p. 738.
Berger et al., *JACS*, vol. 73, No. 9, 1951, pp. 4084–4085.
Bryant et al., *J. Of The Chemical Society*, Dec. 1959, p. 3870.

*Primary Examiner*—Delbert R. Phillips
*Assistant Examiner*—F. T. Moezie
*Attorney, Agent, or Firm*—Toren, McGeady, Stanger, Goldberg & Kiel

[57] ABSTRACT

The invention relates to a selective process for the preparation of N-L-α-aspartyl-L-phenylalanine-1-lower alkyl ester which comprises:
A. reacting an L-aspartic acid 4-arylmethyl ester with a
  (i) 1,3-diketone; or
  (ii) acylacetic ester;
in the presence of a base to form the salt of
  (i') L-N-(1-alkyl-2-acyl-vinyl)-aspartic acid 4-arylmethyl ester; or
  (ii') L-N-(1-alkyl-2-alkoxycarbonyl-vinyl)-aspartic acid 4-arylmethyl ester,
and then either:
(1) reacting salt (i') or (ii') with an organic or inorganic acid halide having the formula X-A, wherein X represents a halogen and A has the meaning indicated hereinafter, or with an acid anhydride to form

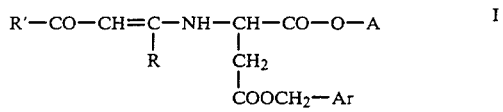

wherein
R represents an alkyl radical with 1 to 6 carbon atoms;
R' represents an alkyl or alkoxy radical with 1 to 6 carbon atoms;
Ar represents the phenyl, nitrophenyl, halogenphenyl or alkylphenyl radical; and
A represents an acyl with 2 to 12 carbon atoms, alkoxycarbonyl with 2 to 12 carbon atoms, or a phosphoric acid, phosphorous acid, sulfuric acid, sulfurous acid or sulfonic acid radical;
and reacting ester (I) with an L-phenylalanine lower alkyl ester; or
(2) reacting a salt of (i') or (ii') with a phosphorazo-L-phenyl lower alkyl ester; to form
  (i'') N-L-α-N'-(1-alkyl-2-acyl-vinyl)-aspartyl-L-phenylalanine-1-lower alkyl-4-arylmethyl ester; or
  (ii'') N-L-α-N'-(1-alkyl-2-alkoxycarbonyl)aspartyl-L-phenylalanine-1-lower alkyl-4-arylmethyl ester;
B. reacting (i'') or (ii'') with a strong acid to split off the respective N-(1-alkyl-2-acyl-vinyl) or N-(1-alkyl-2-alkoxycarbonyl-vinyl) protective group and produce:
  (iii) N-L-α-aspartyl-L-phenylalanine-1-lower alkyl-4-(arylmethyl)ester; and
C. subjecting ester (iii) to catalytic hydrogenation to selectively split off the 4-(arylmethyl)-ester group and leave the N-L-α-aspartyl-L-phenylalanine-1-lower alkyl ester product.

Novel intermediates for the synthesis are also disclosed.

13 Claims, No Drawings

PROCESS FOR THE PREPARATION OF LOWER ALKYL ESTERS OF N-L-α-ASPARTYL-L-PHENYLALANINE AND OF NEW INTERMEDIATES FOR THEIR PREPARATION

BACKGROUND OF THE INVENTION

1. Field of the Invention

The invention relates to a method for the preparation of lower alkyl esters of N-L-α-aspartyl-L-phenylalanine.

2. Description of the Prior Art

Lower alkyl esters of N-L-α-aspartyl-L-phenylalanine, especially the N-L-α-aspartyl-L-phenylalanine-1-methyl ester, which is called α-aspartame, are sought after as low calorie, well tolerated sweeteners.

Numerous processes for the preparation of α-aspartame and its homologous esters are described in the literature. These are either very complicated and therefore unsuitable for use on an industrial scale, or they are not specific and lead to a mixture of α- and β-aspartame.

According to most of the known processes for the preparation of α-aspartame and its homologs, L-aspartyl anhydride, either protected at the nitrogen atom or unprotected, is reacted with the desired L-phenylalanine alkyl ester approximately as shown below:

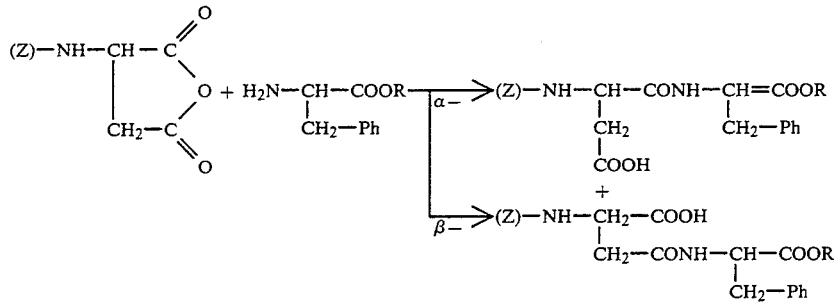

After the protective group Z is split off, a mixture α- and β-form of the product is obtained.

Attempts to influence the mixture ratio in favor of α-aspartame by suitable reaction conditions have met with only moderate success. Since only the α-form can be used as a sweetener, the economics of the manufacturing process become dramatically worse if the formation of the β-form is not suppressed.

Methods for the preparation of selective α-aspartame and its homologous esters start out from the known L-aspartic acid N-carboxylic acid anhydride

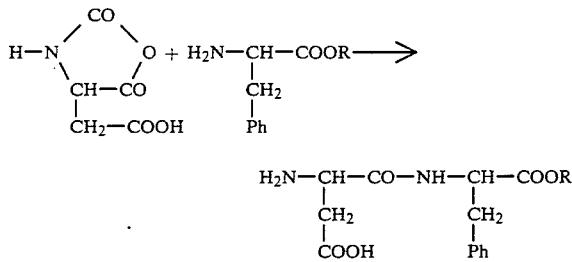

As the reaction outlined above clearly shows, this leads selectively to α-aspartame. The instability of the anhydride mentioned however has made the industrial application of this theoretically simple process impossible until now.

A further selective method was described by Davey, et al, J. Chem. Soc. (Org) 1966(5), 555–66. According to this method, α-trichlorophenyl-β-benzyl-N-benzyloxycarbonyl-L-aspartate is reacted with an L-phenylalanine ester and the product obtained is subsequently split hydrogenolytically. A similar synthesis, based on α-p-nitrophenyl-β-benzyl-N-benzyloxycarbonyl-L-aspartate is described in French Pat. No. 1,577,545. The crucial disadvantage of the two last mentioned methods is the high cost of producing the N-carbobenzoxy-protected asymmetric diester of L-aspartic acid. Various authors have described the reaction of β-benzyl-N-benzyloxycarbonyl-L-aspartic acid with L-phenylalanine methyl ester in the presence of N,N'-dicyclohexylcarbodiimide as a condensation agent. This leads selectively to β-benzyl-N-benzyloxycarbonyl-L-aspartyl-L-phenylalanine ester. However, this method is not suitable for industrial production since the starting material as well as the condensation agent is too expensive.

Recently, Vinick et al, Tetrahedron Letters 23 (13), 1315–19 (1982) and U.S. Pat. No. 4,256,897 described a selective process which is based on the use of L-aspartic acid N-thiocarboxy anhydride as an intermediate. This process is disadvantageous because it is accompanied by strong odors and therefore is not very suitable for the preparation of a food additive.

Consequently, there still is a considerable need for an economic, selective process for the preparation of α-aspartame and its homologous esters.

SUMMARY OF THE INVENTION

We have discovered a new method for the selective preparation of lower alkyl esters of N-L-α-aspartyl-L-phenylalanine which is technically uncomplicated, inexpensive to carry out and does not exhibit the other disadvantages of the previously known processes.

More particularly, the inventive process is based on a new combination of two steps:

1. the use of a simple and selectively removable protective group on the β-carboxyl function of L-aspartic acid; and
2. the use of an inexpensive and easily removable protective group on the amino function of L-aspartic acid.

The inventive method is characterized by the fact that the β-benzyl ester or a substituted β-benzyl ester of L-aspartic acid is used as starting material and that a 1-alkyl-2-acyl-vinyl group, for example, the 1-methyl-2-acetyl-vinyl or the 1-methyl-2-ethoxycarbonylvinyl group is used to protect the amino group. The starting products, the L-aspartic acid 4-arylmethyl ester, for example, L-aspartic acid β-benzyl ester, can be synthesized directly and in relatively good yield by esterifying L-aspartic acid with benzyl alcohol or a substituted benzyl alcohol in the presence of an acid.

As reagent for the formation of the aforementioned protective group on the amino function of L-aspartic acid, the inexpensive commercial products, acetylacetone, acetoacetic ester and their homologs, may, for example, be used. The invention therefore achieves a new, selective and economic process for the preparation of α-aspartame and its homologous esters.

The process of the present invention is carried out by:
(a) reacting an L-aspartic acid 4-arylmethyl ester with a 1,3-diketone or acylacetic ester in the presence of a base, reacting the salt of L-N-(1-alkyl-2-acyl-vinyl- or 1-alkyl-2-alkoxycarbonyl-vinyl)-aspartic acid 4-arylmethyl ester, which is formed in the first reaction, with an organic or inorganic acid halide having the formula X-A, wherein X represents a halogen atom, such as, chlorine or bromine, or with an acid anhydride, and reacting the product of this reaction which is the reactive anhydride of L-N-(1-alkyl-2-acyl-vinyl or 1-alkyl-2-alkoxycarbonyl-vinyl)-aspartic acid 4-arylmethyl ester having the formula I:

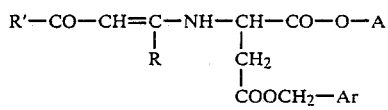

wherein
R represents an alkyl radical with 1 to 6 carbon atoms;
R' represents an alkyl or alkoxy radical with 1 to 6 carbon atoms;
Ar represents the phenyl radical or a nitro-, halogen- or alkylphenyl radical;
A represents an acyl or alkoxycarbonyl radical with 2 to 12 carbon atoms or a phosphoric, phosphorous, sulfuric, sulfurous or sulfonic acid;
with an L-phenylalanine lower alkyl ester; and
(b) reacting a salt of L-N-(1-alkyl-2-acyl-vinyl or 1-alkyl-2-alkoxycarbonyl-vinyl)-aspartic acid 4-arylmethyl ester with a phosphorazo-L-phenyl lower alkyl ester, and treating the N-L-α-N'-(1-alkyl-2-acyl-vinyl or 1-alkyl-2-alkoxycarbonyl-vinyl)-aspartyl-L-phenylalanine-1-lower alkyl-4-arylmethyl-ester, obtained in step (a) or (b) above, with a strong acid, whereby the N-(1-alkyl-2-acyl-vinyl or 1-alkyl-2-alkoxycarbonyl-vinyl) protective group is split off, and then subjecting the N-L-α-aspartyl-L-phenylalanine-1-lower alkyl 4-arylmethyl ester to a catalytic hydrogenation, whereby the 4-arylmethyl ester group is selectively split and the N-L-aspartyl-L-phenylalanine 1-lower alkyl ester is retained.

A further object of the invention is the production of the new intermediates, the N-L-α-N'-(1-alkyl-2-acyl-vinyl- or 1-alkyl-2-alkoxycarbonyl-vinyl)-aspartyl-L-phenylalanine 1-lower alkyl-4-arylmethyl esters having the formula II

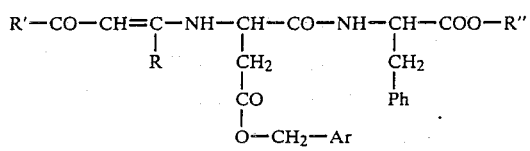

wherein:
R represents an alkyl radical with 1 to 6 carbon atoms;
R' represents an alkyl or alkoxy radical with 1 to 6 carbon atoms;
Ar represents the phenyl radical or a nitro-, halogen- or alkylphenyl radical; and
R" represents the methyl radical or a lower alkyl radical with 2 to 4 carbon atoms.

DESCRIPTION OF THE PREFERRED EMBODIMENT

As starting materials for the process, the L-aspartic acid 4-phenylmethyl ester or a substituted phenylmethyl ester may be used, such as, for example, the 2-nitro-phenylmethyl, 3-nitro-phenylmethyl, 4-nitro-phenylmethyl, the 2-chloro-phenylmethyl, 3-chloro-phenylmethyl, 4-chloro-phenylmethyl, 3,5-dichloro-phenylmethyl, 2,4-dichloro-phenylmethyl, the 2-tolylmethyl, 3-tolylmethyl, 4-tolylmethyl ester, the 3,5-dimethylphenylmethyl ester and the 2,4,6-trimethylphenylmethyl ester.

As reagent for the formation of the protective group on the amino function, a 1,3-diketone or an acetoacetic ester is used inventively. Inexpensive commercial products, such as, acetylacetone, methyl, ethyl, or isopropyl ester of acetoacetic acid, propionylacetone, butyrylacetone and propionylacetic acid alkyl esters may also be used in the same or a similar manner. However, very little advantage, if any, is gained from using these less readily accessible reagents.

Suitable bases for forming a salt with the α-carboxyl function include alkali hydroxides, such as, sodium hydroxide, potassium hydroxide, lithium hydroxide, or tertiary amines, such as, trimethylamine, triethylamine, tripropylamine, tributylamine, methyldiethylamine, diethylpropylamine, dimethylisopropylamine, N-methylpyrrolidine, N-methylpiperidine, and N-methylmorpholine.

Suitable organic or inorganic acid halides having the formula X-A and acid anhydrides for the formation of the mixed acid anhydrides of formula I include:
carbonic half ester chlorides, such as, the methyl, ethyl, propyl, isopropyl, butyl, isobutyl, sec.-butyl, t-butyl, pentyl, nitrophenyl, chlorophenyl, tolyl, phenylmethyl, or phenylethyl esters of chloroformic acid;
fatty acid halides, such as, acetyl chloride, propionyl bromide, 2-methyl-propionyl chloride, butyryl chloride, valeryl chloride, isovaleryl chloride, pivalyl chloride, pivalyl bromide;
phosphoric and phosphorous acid halides, such as, for example, phosphorus oxychloride, ethyl dichlorophosphite, dimethyl chlorophosphite, diethyl chlorophosphite, ethylene chlorophosphite, o-phenylene chlorophosphite;
halides of sulfuric, sulfurous and sulfonic acids, such as, sulfuryl chloride, thionyl chloride, methanesulfonyl chloride, toluenesulfonyl chloride and benzenesulfonyl chloride; and acid anhydrides, such as, sulfur trioxide, 2-sulfobenzoic anhydride, 3-sulfopropionic anhydride, tetraethyl pyrophosphite and bis-1,2-phenylene pyrophosphite.

Suitable as the 1-phenylalanine lower alkyl esters which are reacted with the mixed acid anhydride of formula I, are L-phenylalanine methyl ester, as well as the ethyl, propyl, isopropyl or butyl esters thereof.

As the strong acid for splitting off the N-(1-alkyl-2-acyl-vinyl or 1-alkyl-2-alkoxycarbonyl-vinyl) protective group, hydrochloric acid, nitric acid, sulfuric, phosphoric and formic acid can be used.

The following examples illustrate the invention:

EXAMPLE 1

(A) L-Aspartic acid 4-phenylmethyl ester (22.3 g, 0.1 mole) is suspended in 60 ml of benzyl alcohol and mixed with 10.4 ml acetylacetone (0.1 mole). While stirring, a solution of 6.59 g of potassium hydroxide (85%–0.1 mole) in 50 ml of benzyl alcohol is added dropwise during 1 hour, the temperature being maintained at 60° to 65° C. Stirring is continued for further 2 hours at this temperature. The solution is then cooled to room temperature and the product formed is precipitated by addition of diethyl ether or isolated by evaporating the reaction solution under vacuum and taking up the residue in ethyl acetate.

After filtering and drying, 34.1 g of the potassium salt of L-N-(1-methyl-2-acetyl-vinyl)-aspartic acid 4-phenylmethyl ester, corresponding to 99% of the theoretical yield, are obtained.

Melting point: 101° to 105° C. with decomposition.

Equivalent weight: calculated: 343.4, found: 348.

(B) The potassium salt of L-N-(1-methyl-2-acetyl-vinyl)-aspartic acid 4-phenylmethyl ester (13.7 g, 0.04 moles) is suspended in 100 ml of ethyl acetate and mixed with 0.55 ml of triethylamine. The suspension obtained is reacted at −15° C. with 3.8 ml of ethyl chloroformate (0.04 moles). The mixed anhydride of L-N-(1-methyl-2-acetyl-vinyl)-aspartic acid 4-phenylmethyl ester and ethoxycarbonic acid is formed. While stirring at −10° C., a solution of 0.04 moles of L-phenylalanine methyl ester (prepared from 8.6 g of L-phenylalanine methyl ester hydrochloride (0.04 moles) and 5.54 ml of triethylamine (0.04 moles) in 50 ml of ethyl acetate) is added to the above-described reaction solution. Stirring is continued for several hours at room temperature.

The reaction solution is mixed with 20 ml of 5N hydrochloric acid and stirred vigorously. The phases are now separated. The ethyl acetate phase is evaporated to dryness under vacuum. The oily residue is triturated with dilute nitric acid, during which process crystallization takes place. The product so obtained (15 g) consists of the nitrate of N-L-α-aspartyl-L-phenylalanine-1-methyl-4-(phenylmethyl)-ester.

Equivalent weight: calculated: 447.45, found: 452.5.

(C) N-L-α-aspartyl-L-phenylalanine-1-methyl-4-(phenylmethyl)-ester nitrate (5 g, 0.011 moles) in 75 ml of methanol containing 6 ml of 2N hydrochloric acid is hydrogenated at room temperature in the presence of 0.5 g of a 5% palladium on charcoal catalyst. The catalyst is filtered off and the filtrate is evaporated to dryness. The residue is triturated with water containing sodium bicarbonate. The N-L-α-aspartyl-L-phenylalanine-1-methyl ester formed is filtered off and dried. α-Aspartame, which melts at 246° C. after recrystallization from water, is obtained in a 90% yield (2.9 g).

EXAMPLES 2 to 8

α-Aspartame is obtained in a similar manner when the following are used as starting materials:
2. L-aspartic acid 4-(2-nitrophenylmethyl)-ester
3. L-aspartic acid 4-(3-nitrophenylmethyl)-ester
4. L-aspartic acid 4-(4-nitrophenylmethyl)-ester
5. L-aspartic aicd 4-(4-chlorophenylmethyl)-ester
6. L-aspartic acid 4-(2,4-chlorophenylmethyl)-ester
7. L-aspartic acid 4-(4-tolylmethyl)-ester
8. L-aspartic acid 4-(3,5-dimethylphenylmethyl)-ester.

EXAMPLES 9 to 23

Instead of the ethyl chloroformate of Example 1B, it is also possible to use the following as starting materials:
9. methyl chloroformate
10. propyl chloroformate
11. isobutyl chloroformate
12. sec.-butyl chloroformate
13. benzyl chloroformate
14. phenyl chloroformate
15. 2-methylpropionyl chloride
16. isovaleryl chloride
17. pivaloyl bromide
18. phosphorus oxychloride
19. diethyl chlorophosphite
20. sulfonyl chloride
21. methanesulfonyl chloride
22. 2-sulfobenzoic anhydride
23. tetraethyl pyrophosphite.

EXAMPLE 24

(A) The potassium salt of L-N-(1-methyl-2-acetyl-vinyl)-aspartic acid 4-phenylmethyl ester (51.5 g, 0.15 moles) is suspended in 350 ml of ethyl acetate and mixed with 2 ml of triethylamine. Pivaloyl chloride (18.1 g, 0.15 moles) is added dropwise, with stirring and at −15° C. to the suspension obtained. The mixed anhydride of L-N-(1-methyl-2-acetyl-vinyl)-aspartic acid 4-phenylmethyl ester and pivalic acid of formula I, in which A represents $(CH_3)_3C-CO-$ is formed. Stirring is continued for a further 10 to 30 minutes, after which a solution of 0.15 moles of L-phenylalanine methyl ester in 170 ml of ethyl acetate is allowed to run in at −10° to −15° C. over a period of 1 hour. Stirring is continued for some hours at −15° C. The suspension formed is filtered at room temperature. The filtrate is extracted with aqueous sodium bicarbonate solution and with water.

The ethyl acetate solution obtained contains N-L-α-N'-(1-methyl-2-acetyl-vinyl)-aspartyl-L-phenylalanine-1-methyl-4-(phenylmethyl)-ester.

Thin-layer chromatography (TLC) on silica gel, with a developing solvent of toluene/ethyl acetate/isopropanol/2N acetic acid=2:7:7:4, $R_f$=0.83.

(B) The solution obtained in (A) is treated for 1 to 1½ hours with 150 ml of 2N hydrochloric acid, during which time the protective group is split off. The aqueous phase is removed. The organic ethyl acetate phase dried and evaporated completely. Acetylacetone and ethylacetate can be recovered from the distillate.

The residue from the evaporation (64.3 g corresponding to 101.8% of the theoretical yield) consists of the hydrochloride addition salt of N-L-α-aspartyl-L-phenylalanine-1-methyl-4-(phenylmethyl)-ester.

Melting point (after crystallization from ethyl acetate): 160° to 165° C.

$[\alpha]_D^{20}$= −6.0° (c=4% in 15N formic acid).

TLC on silica gel: developing solvent of acetonitrile/dioxane/water=9:1:4. $R_f=0.63$; spot developed with ninhydrin.

(C) N-L-α-aspartyl-L-phenylalanine-1-methyl-4-(phenylmethyl)-ester hydrochloride (50 g, 0.119 moles) is hydrogenated in methanol at room temperature and normal pressure in the presence of 1 g of a 5% palladium on charcoal catalyst. After the calculated amount of hydrogen has been consumed, the hydrogenation comes to a halt. The catalyst is filtered off and the filtrate is evaporated. The residue is stirred with 400 ml of water and adjusted to a pH of 4.2 by the addition of 2N sodium hydroxide.

The precipitated N-L-α-aspartyl-L-phenylalanine-1-methyl ester hydrate (33.5 g corresponding to 90% of the theoretical yield) melts at 245° C.–247° C. $[\alpha]_D^{20}=+15°$ (c=4% in 15N formic acid).

TLC on silica gel developed with acetonitrile/dioxane/water=9:1:4. $R_f=0.4$; spot developed with ninhydrin.

Equivalent weight: calculated: 312.33, found: 315.36.

EXAMPLES 25 to 31

α-Aspartame is obtained in much the same way as described in Example 1, when acetylacetone is replaced by:
25. ethyl acetoacetate
26. methyl acetoacetate
27. isopropyl acetoacetate
28. ethyl propionylacetate
29. isopropyl propionylacetate
30. propionylacetone
31. butyrylacetone.

EXAMPLE 32

(A) L-phenylalanine methyl ester (10.75 g, 0.06 moles), in 160 ml of dioxane and 10.7 g of pyridine, is stirred at ~10° C. with 4.1 g of phosphorus trichloride (0.03 moles). The phosphorazo compound formed (Houben-Weyls "Methoden der organischen Chemie"- Method of Organic Chemistry-, Vol. 15/2, 237–240 (1974)) precipitates out. Stirring is continued for a further 1 to 3 hours at room temperature, after which time 20.6 g of the potassium salt of L-N-(1-methyl-2-acetyl-vinyl)-aspartic acid 4-phenylmethyl ester (0.06 moles) is added and the reaction is stirred at first at room temperature and then for 5 hours under reflux. The reaction solution is cooled and filtered and the filtrate is evaporated to dryness. According to thin-layer chromatography and liquid chromatography, the residue of the evaporation (20 g) consist mainly of N-L-α-aspartyl-L-phenylalanine-1-methyl-4-(phenylmethyl)-ester.

(B) The residue (10 g) is subjected to hydrogenolysis as in Example 24C, α-aspartame being obtained.

We claim:
1. A process for the selective preparation of N-L-α-aspartyl-L-phenylalanine-1-lower alkyl ester which comprises:
A. reacting an L-aspartic acid 4-arylmethyl ester with a
   (i) 1,3-diketone; or
   (ii) acylacetic ester;
   in the presence of a base to form the salt of
   (i') L-N-(1-alkyl-2-acyl-vinyl)-aspartic acid 4-arylmethyl ester; or
   (ii') L-N-(1-alkyl-2-alkoxycarbonyl-vinyl)-aspartic acid 4-arylmethyl ester,
   and then either:
   (1) reacting salt (i') or (ii') with an organic or inorganic acid halide having the formula X-A, wherein X represents a halogen and A has the meaning indicated hereinafter, or with an acid anhydride to form

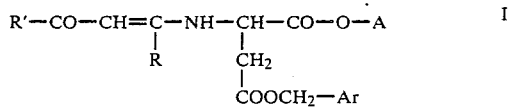

wherein
R represents an alkyl radical with 1 to 6 carbon atoms;
R' represents an alkyl or alkoxy radical with 1 to 6 carbon atoms;
Ar represents the phenyl, nitrophenyl, halogenphenyl or alkylphenyl radical; and
A represents an acyl with 2 to 12 carbon atoms, alkoxycarbonyl with 2 to 12 carbon atoms, or a phosphoric acid, phosphorous acid, sulfuric acid, sulfurous acid or sulfonic acid radical;
and reacting ester (I) with an L-phenylalanine lower alkyl ester;
   (2) reacting a salt of (i') or (ii') with a phosphorazo-L-phenyl lower alkyl ester; to form
   (i'') N-L-α-N'-(1-alkyl-2-acyl-vinyl)-aspartyl-L-phenylalanine-1-lower alkyl-4-arylmethyl ester; or
   (ii'') N-L-α-N'-(1-alkyl-2-alkoxycarbonyl)-aspartyl-L-phenylalanine-1-lower alkyl-4-arylmethyl ester;
B. reacting (i'') or (ii'') with a strong acid to split off the respective N-(1-alkyl-2-acyl-vinyl) or N-(1-alkyl-2-alkoxycarbonyl-vinyl) protective group and produce:
   (iii) N-L-α-aspartyl-L-phenylalanine-1-lower alkyl-4-(arylmethyl)ester; and
C. subjecting ester (iii) to catalytic hydrogenation to selectively split off the 4-(arylmethyl)-ester group and leave the N-L-α-aspartyl-L-phenylalanine-1-lower alkyl ester product.

2. The process of claim 1 wherein the starting ester in step A is a 4-phenylmethyl ester or a substituted phenylmethyl ester.

3. The process of claim 1 wherein the starting ester is selected from the group consisting of the 2-nitro-phenylmethyl, 3-nitro-phenylmethyl, 4-nitro-phenylmethyl, the 2-chloro-phenylmethyl, 3-chloro-phenylmethyl, 4-chloro-phenylmethyl, 3,5-dichloro-phenylmethyl, 2,4-dichloro-phenylmethyl, the 2-tolylmethyl, 3-tolylmethyl, 4-tolylmethyl ester, the 3,5-dimethylphenylmethyl ester and the 2,4,6-trimethylphenylmethyl ester.

4. The process of claim 1 wherein the 1,3-diketone or acetoacetic ester is selected from the group consisting of acetylacetone, the methyl, ethyl, or isopropyl ester of acetoacetic acid, propionylacetone, butyrylacetone and propionylacetic acid alkyl esters.

5. The process of claim 1 wherein the base used in step A is an alkali hydroxide or a tertiary amine.

6. The process of claim 1 wherein the base is selected from the group consisting of sodium hydroxide, potassium hydroxide, lithium hydroxide, trimethylamine, triethylamine, tripropylamine, tributylamine, methyldiethylamine, diethylpropylamine, dimethylisopropylamine, N-methylpyrrolidine, N-methylpiperidine, and N-methylmorpholine.

7. The process of claim 1 wherein the inorganic acid is selected from the group consisting of carbonic half ester chlorides, fatty acid halides, phosphoric or phosphorous acid halides, halides of sulfuric, sulfurous, or sulfonic acids.

8. The process of claim 7 wherein the acid is selected from the group consisting of the methyl, ethyl, propyl, isopropyl, butyl, isobutyl, sec.-butyl, t-butyl, pentyl, nitrophenyl, chlorophenyl, tolyl, phenylmethyl, or phenylethyl esters of chloroformic acid; acetyl chloride, propionyl bromide, 2-methyl-propionyl chloride, butyryl chloride, valeryl chloride, isovaleryl chloride, pivalyl chloride, pivalyl bromide; phosphorus oxychloride, ethyl dichlorophosphite, dimethyl chlorophosphite, diethyl chlorophosphite, ethylene chlorophosphite, o-phenylene chlorophosphite; sulfuryl chloride, thionyl chloride, methanesulfonyl chloride, toluenesulfonyl chloride and benzenesulfonyl chloride.

9. The process of claim 1 wherein the acid anhydride is selected from the group consisting of sulfur trioxide, 2-sulfobenzoic anhydride, 3-sulfopropionic anhydride, tetraethyl pyrophosphite and bis-1,2-phenylene pyrophosphite.

10. The process of claim 1 wherein the 1-phenylalanine lower alkyl ester used in step A (1) is selected from the group consisting of the methyl, ethyl, propyl, isopropyl, and butyl esters.

11. The process of claim 1 wherein the strong acid used in step B is selected from the group consisting of hydrochloric acid, nitric acid, sulfuric, phosphoric and formic acid.

12. N-L-α-N'-(1-alkyl-2-acyl-vinyl)- or (1-alkyl-2-alkoxycarbonyl-vinyl)-aspartyl-L-phenylalanine 1-alkyl-4-arylmethylesters having the formula:

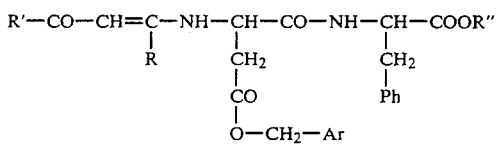

wherein
R represents an alkyl radical with 1 to 3 carbon atoms;
R' represents an alkyl or alkoxy radical with 1 to 3 carbon atoms;
Ph represents phenyl;
Ar represents the phenyl radical or a halogen- or alkylphenyl radical; and
R" represents a lower alkyl radical with 1 to 3 carbon atoms.

13. N-L-α-N'-(1-methyl-2-acetyl-vinyl)-aspartyl-L-phenylalanine-1-methyl-4-phenylmethyl-ester having the formula:

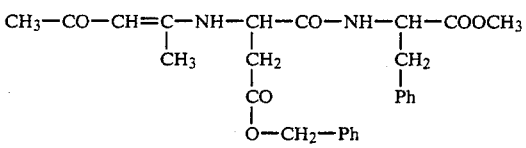

wherein Ph is phenyl.

* * * * *